United States Patent [19]

Garabedian

[11] Patent Number: Plant 5,912

[45] Date of Patent: Mar. 24, 1987

[54] PLUM TREE, "RANCH 9-GOLDEN"

[76] Inventor: John M. Garabedian, 3104 E. Huntington Blvd., Fresno, Calif. 93747

[21] Appl. No.: 766,556

[22] Filed: Aug. 19, 1985

[51] Int. Cl.[4] ..... A01H 5/03
[52] U.S. Cl. ..... Plt./38
[58] Field of Search ..... Plt./38

*Primary Examiner*—Robert E. Bagwill
*Attorney, Agent, or Firm*—Worrel & Worrel

[57] ABSTRACT

A new and distinct variety of plum tree which is somewhat similar to the Roysum Plum Tree (U.S. Plant Pat. No. 2,619) and the Angeleno Plum Tree (U.S. Plant Pat. No. 2,747) concurrently with which it bears fruit which is characteristically a full dark Purplish-Red color of uniform globular shape and by its firm, Golden Yellow flesh which has Purplish-Red pigment diffused into the flesh next to the fruit skin, and further characterized by the extreme tightness with which the flesh fibers adhere to the stone surface.

1 Drawing Figure

BACKGROUND OF THE NEW VARIETY

The present invention relates to a plum tree known as the "Ranch 9-Golden", and more particularly to a plum tree which bears fruit at substantially the same time as the "Roysum" Plum Tree (U.S. Plant Pat. No. 2,619), which matures at approximately the same season, and the Angeleno Plum Tree (U.S. Plant Pat. No. 2,747) to which it is similar in characteristics, but from which it is distinguished in being a full, dark purplish-red color, with firm, golden yellow flesh that has red pigment diffused in the flesh next to the fruit skin, and is further characterized by a heavy blue-gray bloom and its extreme clingstone nature.

The applicant, in an effort to upgrade his fruit products, has germinated thousands of plum seeds, of random parentage, grown the resultant seedlings to maturity, and carefully studied the characteristics of the progeny to try and discover new and superior varieties of plums. The subject variety was discovered as a result of this procedure.

The factors that contribute toward the commercial acceptance and the success of any variety of plum are numerous. However, it is well known that the visual appearance of the plum is one of primary-motivating factors involved in a consumer's decision to purchase one type of plum rather than another. It is well known that a plum that combines the desirable characteristics of visual aesthetic appeal with the complimentary attribute of having a firm, delicate-flavored flesh, is one which possesses a strong chance of becoming the object of repeated purchase by individual consumers.

It has long been recognized as desirable to provide a plum tree variety which bears fruit that has a full, dark purplish-red color, which is of uniform size and regular shape and which is characterized by a firm, golden yellow flesh. This is particularly important when the subject variety ripens at nearly the same time as numerous other varieties which have nearly similar attributes. These distinctive characteristics, therefore, allow the subject variety to have an advantage in competition with those plums that are maturing at approximately the same time.

ORIGIN AND ASEXUAL REPRODUCTION OF THE NEW VARIETY

The seedling of the present variety was the offspring of unknown parents and was germinated by the applicant and grown with thousands of other seedlings in 1977, at his ranch located at the corner of Kings Canyon Road and Fowler Avenue in Fresno, County of Fresno, State of California. When the unique qualities of the subject variety were detected and appreciated, the applicant asexually reproduced the instant variety by budding scions of the seedling into stock plum trees, then planted on Ranch No. 9 located at the south east corner of Fowler Avenue and Belmont Avenue in Fresno, Calif. in 1980. The budded progeny were grown at the aforementioned ranch until it was determined that the new variety dependably and accurately reproduced the superior characteristics observed by the applicant in the original seedling.

BRIEF DESCRIPTION OF THE DRAWING

The accompanying drawing is a color photograph of a characteristic twig bearing typical leaves, a cluster of two plums showing their external coloration sufficiently mature for harvesting and shipment, three mature plums of the color when matured on the trees, a plum halved transversely of the suture plane to illustrate the flesh coloration, and three stones, all of the subject variety.

DETAILED DESCRIPTION

Referring more particularly to the pomological details of this new and distinct variety of plum tree, the following has been observed under the ecological conditions prevailing in the designated orchards near Fresno, Calif. All major color code designations are by reference to the Munsell Limit Color Cascade. Common color names are also used occasionally.

TREE

Size: Medium, depending upon pruning practices.
Vigor: Medium.
Figure: Spreading, open, and vase-formed.
Productivity: Productive.
Regularity of bearing: Regular.

Trunk:
*Thickness.*—Medium.
*Texture of bark.*—Medium.
Branches:
*Thickness.*—Medium.
*Texture.*—Medium.
*Color.*—Brown (MCC 32-15), striated with lighter dull brown areas.
*Lenticels.*—Few in number, medium in size.

LEAVES

Shoot:
*Size.*—Medium.
*Length.*—10.71±0.93 cm.
*Width.*—4.83±0.47 cm.
*Form.*—Ovate, acuminate, acutely pointed.
*Color.*—Medium Green on ventral surface (MCC 20-14 to 20-14); dorsal surface somewhat lighter green.
*Thickness.*—Medium.
*Texture.*—Nearly smooth.
*Marginal form.*—Crenate.
*Petiole.*—Length — medium, 1.55±0.33 cm.; medium in thickness.
*Glands.*—Variable in number between 0 and 3; usually opposite; small; globose; green; one or more positioned on the petiole near the base of the blade.
*Stipules.*—Linear and ephemeral.
Spur:
*Size.*—Medium.
*Length.*—11.09±0.09 cm.
*Width.*—3.86±0.36 cm.
*Form.*—Narrowly obovate; acuminate; abruptly pointed.
*Thickness.*—Medium.
*Color.*—Medium Green (MCC 20-14 or 21-14).
*Texture.*—Nearly smooth.
*Marginal form.*—Crenate.
*Petiole.*—Long; Length — 2.17±0.33 cm.; thickness — medium to slender.
*Glands.*—Variable in number, from 0 through 2; usually opposite; small; globose; green; one or more positioned at the base of the blade.
*Stipules.*—Completely lacking.
Flower buds: Small, short, plump, free and glabrous.
Flowers: Medium in size and white.
*Date of first bloom.*—Feb. 28, 1984.
*Date of full bloom.*—Mar. 8, 1984; date of bloom is average as compared with other varieties.

FRUIT

Maturity when described: Hard ripe, September 8.
Size: Uniform, small to medium.
*Axial diameter.*—4.72±0.19 cm.
*Diameter transverse in suture plane.*—5.17±0.21 cm.
*Diameter transverse in cheek plane.*—5.30±0.22 cm.
Form: Uniform symmetrical, broadly oval to somewhat oblate.
Suture: A shallow groove extending from the base to the apex; there is a slight depression beyond the pistil point.
Ventral surface: Rounded slightly, and broadly lipped throughout; lips are equal.
Cavity: Flaring, rounded and circular; the suture shows on one side.
*Depth.*—0.64±0.23 cm.
*Breadth.*—1.60±0.18 cm.
*Markings.*—None.
Base: Broadly rounded.
Apex: Truncated; depressed.
Pistil point: Apical.
Stem: Medium in length; 1.25 cm. through 1.5 cm.; slender to medium in thickness.
Skin: Medium in thickness; tough in texture; tenacious to flesh; no observed tendency to crack in the dry season.
*Color.*—Very dark Purplish-Red (MCC 45-16).
*Bloom.*—Medium Gray (MCC 2-4).
*Dots.*—Few in number, when present, small, round, Light Brown; located on the cheeks medianly; inconspicuous underneath the bloom.
*Down.*—Wanting.
Flesh:
*Color.*—Light Yellow (MCC 29-3), a diffused Medium Red pigment is present next to the skin; cavity color is slightly darker than the flesh.
*Amygdalin.*—Wanting.
*Texture.*—Medium to firm; fine and meaty.
*Fibers.*—Few in number, fine, and tender.
*Ripening.*—Even.
*Flavor.*—Mild and delicate.
*Aroma.*—Wanting.
*Eating quality.*—Good.
*Juice production.*—Scant to moderate.
Stone: Extreme clingstone, adheres very tightly to the flesh over the entire surface; fibers are long.
*Size.*—Medium.
*Length.*—2.33±0.09 cm.
*Breadth.*—1.71±0.06 cm.
*Thickness.*—1.05±0.10 cm.
*Form.*—Oval.
*Base.*—Straight.
*Hilum.*—Narrow oval.
*Apex.*—Rounded, with a sharp, small tip.
*Sides.*—Unequal, with the ventral side being longer.
*Surface.*—Nearly smooth; ridged near the base, which is often elongated.
*Ventral edge.*—Thin, without wing throughout.
*Dorsal edge.*—Narrow with variable depth and variable width groove extending to above center.
*Ridges.*—Continuous.
*Color of stone.*—Light Brown (MCC 31-3).
Use: Market, local and dessert.
Keeping quality: good.
Resistance to insects; Medium.
Resistance to disease: Unknown.
Shipping quality: Good.

Although the new variety of plum tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated my new variety of plum tree, what is claimed as new and desired to be secured by Letters Patent is:

1. A new and distinct variety of plum tree substantially as illustrated and described which is somewhat similar to the Roysum Plum Tree (U.S. Plant Pat. No. 2,619) and the Angeleno Plum Tree (U.S. Plant Pat. No.

2,747) with which it bears fruit which matures at substantially the same season but from which it is distinguished by bearing fruit which is of a full dark Purplish-Red color, of uniform size and regular shape, having a firm, Golden Yellow flesh which has red pigment diffused into the flesh next to the skin and furthermore by a characteristic extreme tightness with which the flesh fibers adhere to the stone surface.

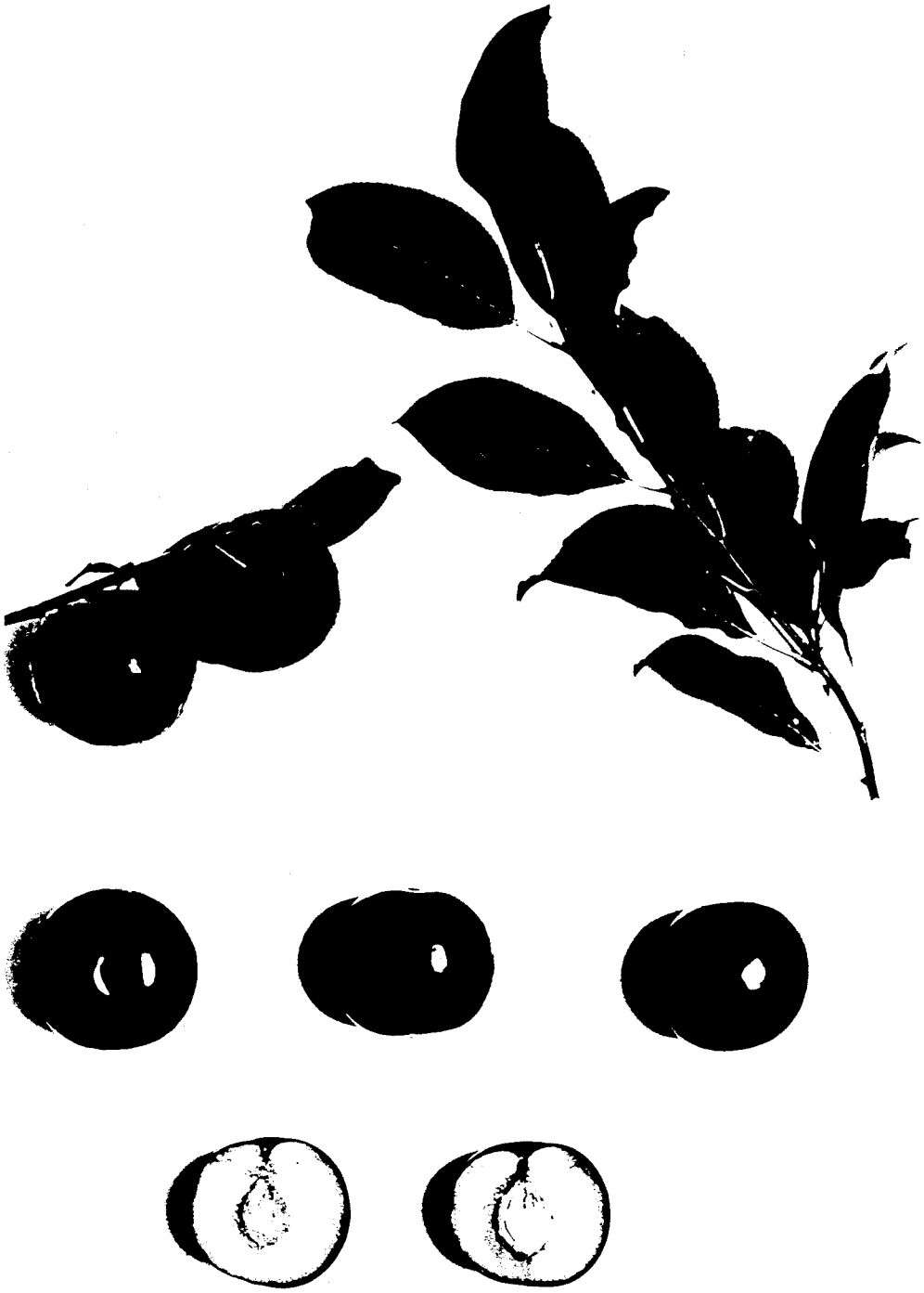

* * * * *